United States Patent
Di Cintio et al.

(10) Patent No.: US 6,960,655 B2
(45) Date of Patent: *Nov. 1, 2005

(54) ARTICLES HAVING AN ODOR CONTROL SYSTEM COMPRISING A CATIONIC POLYSACCHARIDE AND AN ODOR CONTROLLING AGENT

(75) Inventors: Achille Di Cintio, Pescara (IT); Antonella Pesce, Pescara (IT); Giovanni Carlucci, Chieti (IT); Alessandro Gagliardini, Jesi (IT)

(73) Assignee: The Procter & Gamble Company, Cincinnati, OH (US)

( * ) Notice: Subject to any disclaimer, the term of this patent is extended or adjusted under 35 U.S.C. 154(b) by 359 days.

This patent is subject to a terminal disclaimer.

(21) Appl. No.: 10/238,414

(22) Filed: Sep. 10, 2002

(65) Prior Publication Data

US 2003/0022573 A1 Jan. 30, 2003

Related U.S. Application Data

(63) Continuation of application No. PCT/US01/13159, filed on Apr. 24, 2001.

(30) Foreign Application Priority Data

Apr. 25, 2000  (EP) .......................................... 00108064

(51) Int. Cl.⁷ ........................ C08B 37/08; A61F 13/15; A61F 13/20

(52) U.S. Cl. .......................... 536/20; 604/375; 604/378
(58) Field of Search .................. 536/20, 55.1; 604/375, 604/378, 361, 358, 385; 424/412

(56) References Cited

U.S. PATENT DOCUMENTS

| | | | |
|---|---|---|---|
| 5,932,495 A | | 8/1999 | Boney |
| 6,383,960 B1 | * | 5/2002 | Everett et al. ............... 442/392 |

FOREIGN PATENT DOCUMENTS

| | | | | |
|---|---|---|---|---|
| EP | 0811392 | * | 10/1997 | ........... A61L/15/46 |
| EP | 0 811 392 A1 | | 12/1997 | |
| GB | 2 292 526 A | | 2/1996 | |
| WO | WO 91/12029 A1 | | 8/1991 | |
| WO | WO 99/32697 A2 | | 7/1999 | |
| WO | WO 9932697 | * | 7/1999 | |
| WO | WO 99/55393 A1 | | 11/1999 | |
| WO | WO 00/50098 A1 | | 8/2000 | |

* cited by examiner

*Primary Examiner*—James O. Wilson
*Assistant Examiner*—Ganapathy Krishnan
(74) *Attorney, Agent, or Firm*—Bridget D. Murray; Kevin C. Johnson

(57) ABSTRACT

The present invention relates to articles suitable for controlling odors, especially odors associated with bodily fluids, which comprise a cationic polysaccharide, preferably chitosan material, together with an odor controlling agent, preferably an odor absorbent agent and/or a chelating agent. This combination provides synergistic reduced odor control towards malodors associated with bodily fluids like menses.

12 Claims, No Drawings

ARTICLES HAVING AN ODOR CONTROL SYSTEM COMPRISING A CATIONIC POLYSACCHARIDE AND AN ODOR CONTROLLING AGENT

CROSS REFERENCE TO RELATED REFERENCES

This is a continuation of International Application PCT/US01/13159 with an International filing date of Apr. 24, 2001.

FIELD OF THE INVENTION

This invention relates to articles, such as absorbent articles, for controlling odors, especially odors associated with bodily fluids, comprising a cationic polysaccharide, preferably chitosan material, together with an odor-controlling agent.

BACKGROUND OF THE INVENTION

Malodors may be present in the environment from numerous sources both animate and inanimate. Many products and articles are available which aim to avoid or minimize the detection of such odors. In particular, it is particularly desirable to provide odor controlling materials to address the malodors which are generated by the human body, or from bodily fluids such as perspiration, urine, faeces, menstrual fluids, vaginal fluids and the like.

Articles like absorbent articles for example are designed to be worn by humans to absorb bodily fluids, such as urine, menstrual fluid and perspiration, etc. Examples of absorbent articles include sanitary napkins, pantiliners, disposable diapers, incontinence pads, tampons, perspiration pads, nursing pads and the like.

In use, the absorbent articles are known to acquire a variety of compounds, for example volatile fatty acids (e.g. isovaleric acid), ammonia, amines (e.g. triethylamine), sulphur containing compounds (e.g. mercaptans, sulphides), alcohols, ketones and aldehydes (e.g., furaldehyde) which release unpleasant odors. These compounds may be present in the bodily fluid or may be developed by chemical reactions and/or any fluid degradation mechanisms once the bodily fluid is absorbed into the absorbent article like for example a feminine pad. In addition bodily fluids usually contain micro-organisms and/or enzymes that can also generate malodorous by products as a result of degradation mechanisms like putrefactive degradation, acid degradation, proteins degradation, fat degradation and the like. Unpleasant odors, which emanate from absorbent pads when in use, may make the wearer feel self-conscious.

Various odor-controlling materials have been disclosed in the art to combat some of the unpleasant odors referred to above. Indeed solutions have been provided that use different technical approaches like masking, i.e., covering the odor with a perfume, or absorbing the odor already present in the bodily fluids and those generated after degradation.

Most of the focus in the prior art is found on the odor absorption technology. Examples of these types of compounds include activated carbons, clays, zeolites, silicates, starches, cyclodextrine, ion exchange resins and various mixture thereof as for example described in EP-A-348 978, EP-A-510 619, WO 91/12029, WO 91/11977, WO 89/02698, and/or WO 91/12030. All of these types of odor controlling agents are believed to control odor by mechanisms whereby the malodorous compounds and their precursors are physically absorbed by the agents and thus such agents hinder the exit of the odor from articles like absorbent articles. However, such mechanisms are not completely effective as the formation of the odor itself is not prevented and thus odor detection is not completely avoided.

Thus although these materials provide some control of odors associated with bodily fluids, there still exists a need of further improvement in terms of odor control over a wide range of malodorous compounds.

It is an object of the present invention to provide effective odor control over a wide range of malodors. More particularly, it is an object of the present invention to provide articles, especially disposable absorbent articles, which deliver outstanding odor control over a broad spectrum of malodors.

It has now been found that the above needs can be addressed by combining a cationic polysaccharide together with an odor-controlling agent, as the odor control system for an article, preferably a disposable absorbent article.

It has surprisingly been found that the combination of an odor controlling agent, typically an odor absorbent agent (e.g., zeolite and/or cyclodextrin) and/or a chelating agent (e.g., ethylene diamine tetracetate (EDTA)) together with a cationic polysaccharide, preferably chitosan material, in an article, like an absorbent article, typically coming into contact with bodily fluids, results in a synergistic effect in terms of odor control. Indeed this combination gives more odor reduction than the odor reduction associated with the use of one of these two classes of ingredients alone at the same total level (either said odor controlling agent alone or said cationic polysaccharide alone) in an absorbent article contacted with bodily fluids.

Actually the combination of a cationic polysaccharide with an odor-controlling agent in an article herein allows combining odor control mechanisms by which the overall malodor detection is synergistically reduced or even prevented.

Without to be bound by any theory it is believed that cationic polysaccharides, preferably chitosan materials, provide odor control of malodorous components associated with bodily fluid by multiple mechanisms.

Firstly, the odor absorption and retention characteristics of polysaccharides are due to the presence in the polymer structure of ionisable cationic functional groups. These groups are usually ammonium groups, a high proportion of which are in the salt form when the polymer is dry but which undergo dissociation and salvation upon contact with bodily fluid. In the dissociated state, the polymer chain will have a series of functional groups attached to it which groups have the same electric charge (e.g., $-NH_3^+$ $^+H_3N-$) and thus repel one another. This leads to expansion of the polymer structure, which, in turn permits further absorption of negatively charged odorous molecules and thus the control thereof.

Secondly, the positively charged cationic groups of the polysaccharides will interact with negatively charged anionic functionalities present in bodily fluids, like the carboxylic groups of proteins or hydroxylic acid bearing entities like short chain acid (e.g., butyric acid). This will result in the formation of tri-dimensional net between cationic polysaccharides and such molecules with anionic groups (gelification of the bodily fluids). This gelification will entrap most odorous molecules (like lipids, acids) thereby controlling malodor.

Thirdly and more importantly the cationic polysaccharides especially the aminopolysaccharides (chitosan materials) are believed to act as antimicrobial agents. Indeed the polysaccharides with their positively charged cationic groups will interfere with negatively charged surface of microorganism walls, thereby inhibiting the growth of such microorganisms or even killing such microorganisms. These cationic polysaccharides will also interfere with negatively charged surface of enzymes, thereby inactivating the enzymatic activity, which, like the microbial activity, are otherwise responsible for the formation of malodorous components. The cationic polysaccharides like chitosan materials further act by their indirect antimicrobial activity by linking some of the microorganism nutriments like lipids and/or minerals.

Surprisingly, the presence of the cationic polysaccharide, like chitosan material, increases the effectiveness of odor controlling agents like odor absorbent agents. Without to be bound by any theory it is speculated that the cationic polysaccharides herein, typically chitosan materials, control enzymatic and microbial growth and as a consequence the amount of malodorous compounds associated with the enzymatic and microbial activity occurring in bodily fluid. In other words, the cationic polysaccharides reduce or even prevent the formation of malodorous compounds, thereby reducing the total amount of malodor to be controlled. This allows the odor-controlling agent, typically the odor absorbent agent (e.g., zeolite and/or cyclodextrin) to work in reduced amount of active. Actually this results in a more effective as well as a sustained use of the odor-controlling agent herein. Indeed the saturation point of the odor absorbent agents when used in association with the cationic polysaccharides herein will be reached after prolonged periods of use, typically after prolonged wearing time of an absorbent article (pantiliner, pad) coming into contact with bodily fluid, as compared to when used alone in absence of the cationic polysaccharides in the same conditions.

Advantageously it is believed that the odor controlling agents, typically the odor absorbent agents, also help the cationic polysaccharides in reducing malodor by adsorbing not only odor present in the bodily fluids but also volatile odor present in the head space (space between the absorbent article and the urogenital surface). This combination is thus active too towards volatile malodor components, which escape from the bodily fluids and hence would not come in direct contact with the polysaccharides. Actually this combination allows odor control over a wider range of malodorous components, which would otherwise not have been fully controlled by one of these two classes of ingredients used alone.

Surprisingly the presence of a chelating agent on top of the cationic polysaccharide, namely chitosan material, results in increased antimicrobial properties. Without to be bound by any theory it is believed that the chelating agents used herein complete the antimicrobial properties of the cationic polysaccharides, by their indirect antimicrobial activity. Indeed the chelating agents have the ability to link some of the microorganisms nutriments like positively charged growth factors, typically $Ca^{++}$, $K^+$, $Mg^{++}$. Advantageously the combination of these two preventing mechanisms results in a synergistic reduction in odor formation.

In a preferred embodiment herein the disposable absorbent articles have an apertured polymeric film topsheet. This topsheet contributes to further improve the odor control benefit.

In another preferred embodiment herein the disposable absorbent articles have a breathable backsheet. This contributes to a further improved odor control benefit. Even more preferred herein the disposable absorbent articles have both a breathable backsheet and an apertured polymeric film topsheet.

The present invention is preferably directed to disposable absorbent articles like pantiliners, feminine napkins, incontinent pads, diapers, tampons, interlabial pads, perspiration pads, surgical pads, breast pads, human or animal waste management devices and the like. Other articles suitable for use according to the present invention further include articles designed to be contacted with the body such as clothing, bandages, thermal pads, acne pads, cold pads, compresses, surgical pads/dressings and the like, body cleansing articles like impregnated wipes/tissues (e.g. baby wipes, wipes for feminine intimate hygiene), articles for absorbing perspiration such as shoe insoles, shirt inserts, and the like, and articles for animals like litters and the like.

BACKGROUND ART OF THE INVENTION

WO 99/61079 discloses odor reduction for products such as disposable diapers and training pants, sanitary napkins and tampons by the use of triglycerides and polyglycosides to enhance the malodor absorption properties of compositions and substrates such as naturally occurring polymers like chitosan or alginates and synthetic polymers treated with surfactants.

WO 99/32697 discloses that chitosan and chitin-based polymers exhibit increased antimicrobial activity when coated onto the surface of a hydrophobic material such as polypropylene.

None of these references discloses absorbent articles comprising cationic polysaccharides, typically chitosan materials, together with an additional odor controlling agent, typically an odor absorbent agent like zeolite and/or cyclodextrin, or a chelating agent like ethylene diamine tetracetate, let alone that such combinations result in synergistic malodor reduction.

SUMMARY OF THE INVENTION

The present invention relates to an article, preferably a disposable absorbent article, for controlling odors, preferably odors associated with bodily fluids, comprising a cationic polysaccharide and an additional odor-controlling agent. In a preferred embodiment of the invention the article also comprises an absorbent gelling material.

DETAILED DESCRIPTION OF THE INVENTION

By "article" it is meant herein any three-dimensional solid material being able to comprise a cationic polysaccharide and an odor-controlling agent. The term "disposable" is used herein to describe articles, which are not intended to be launched or otherwise restored or reused as an article (i.e., they are intended to be discarded after a single use and, preferably to be recycled, composted or otherwise disposed of in an environmentally compatible manner). The term "absorbent articles" is used herein in a very broad sense including any article able to receive and/or absorb and/or contain and/or retain fluids and/or exudates, especially bodily fluids and/or exudates.

Preferred articles according to the present invention are disposable absorbent articles that are designed to be worn in contact with the body of a user and to receive fluids/exudates from the body, such as pantiliners, sanitary napkins, catamenials, incontinence inserts/pads, diapers, tampons, interlabial pads/inserts, breast pads, human or animal waste management devices and the like. Typically such human urine or faecal management devices comprise a bag having an aperture and a flange surrounding the aperture for preferably adhesive attachment to the urogenital area and/or the perianal area of a wearer. Any faecal or urine management device known in the art is suitable for use herein. Such devices are described in for example WO 99/00084 to WO 99/00092. Other suitable articles according to the present invention also include other articles designed to be placed against or in proximity to the body such as clothing, bandages, thermal pads, acne pads, cold pads, compresses, surgical pads/dressings and the like, articles for absorbing perspiration such as shoe insoles, shirt inserts, perspiration pads and the like, body cleansing articles like impregnated wipes/tissues (e.g. baby wipes, wipes for feminine intimate hygiene), and the like, and articles for animals like litters and the like.

By "bodily fluid and/or bodily exudate" it is meant herein any exudate/fluid produced by human or animal body occurring naturally or accidentally like for instance in the case of skin cutting, including for instance perspiration, urine, menstrual fluids, faeces, vaginal secretions and the like.

Cationic Polysaccharides

According to the present invention the articles comprise as an essential component a cationic polysaccharide or a mixture thereof.

Suitable cationic polysaccharides for use herein are positively charged polysaccharides due to the presence of cationic functional groups. Suitable polysaccharides for use herein include natural and semi-synthetic cationic polysaccharides. Examples of suitable cationic functional groups include primary, secondary or tertiary amine groups or quaternary ammonium groups, which should be present in base form. Preferably quaternary ammonium groups are present. The cationic polysaccharides for use herein might be a fibrous polysaccharide such as cellulose with an excess of quaternary ammonium compound containing at least one group capable of reacting with polysaccharide hydroxyl groups. Such cationic polysaccharides are described in WO 92/19652 and WO 96/17681, herein incorporated by reference. Highly preferred herein are aminopolysaccharides, namely chitin-based materials, chitosan materials and mixture thereof.

By 'chitosan material' it is meant herein chitosans, modified chitosans, crosslinked chitosans and chitosan salts.

Chitosan is a partially or fully deacetylated form of chitin, a naturally occurring polysaccharide. Indeed, chitosan is an aminopolysaccharide usually prepared by deacetylation of chitin (poly-beta (1,4)-N-acetyl-D-glucosamine).

Chitin occurs widely in nature, for example, in the cell walls of fungi and the hard shell of insect and crustaceans. The waste from shrimp-, lobster-, and crab seafood industries typically contains about 10 to about 15 percent chitin and is a readily available source of supply. In the natural state, chitin generally occurs only in small flakes or short fibrous material, such as from the carapace or tendons of crustaceans. There is generally no source, as with cotton in the cellulosics, that forms useful shaped articles without solution and re-precipitation or re-naturing.

More specifically, chitin is a mucopolysaccharide, poly-N-acetyl-D-glucosamine with the following formula:

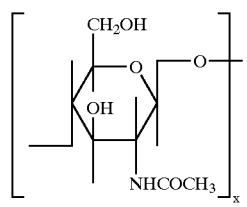

wherein x represents the degree of polymerization. Although x cannot be determined precisely, x is believed to be commonly in the range of from about 30 to about 50,000.

Chitosan is not a single, definite chemical entity but varies in composition depending on the conditions of manufacture. It may be equally defined as chitin sufficiently deacetylated to form soluble amine salts. Chitosan is the beta-(1-4) polysaccharide of D-glucosamine, and is structurally similar to cellulose, except that the C-2 hydroxyl group in cellulose is substituted with a primary amine group in chitosan. The large number of free amine groups makes chitosan a polymeric weak base. Solutions of chitosan are generally highly viscous, resembling those of natural gums.

The chitosan used herein is suitably in relatively pure form. Methods for the manufacture of pure chitosan are well known. Generally, chitin is milled into a powder and demineralized with an organic acid such as acetic acid. Proteins and lipids are then removed by treatment with a base, such as sodium hydroxide, followed by chitin deacetylation by treatment with concentrated base, such as 40 percent sodium hydroxide. The chitosan formed is washed with water until the desired pH is reached.

The properties of the aminopolyssaccharides, especially chitosan, relate to their polyelectrolyte and polymeric carbohydrate character. Thus, chitosan is generally insoluble in water, in alkaline solutions at pH levels above about 6.5, or in organic solvents. It generally dissolves readily in dilute solutions of organic acids such as formic, acetic, tartaric, glycolic, lactic and citric acids, and also in dilute mineral acids, except, for example, sulfuric acid. In general, the amount of acid required to dissolve chitosan is approximately stoichiometric with the amino groups. Since the pKa for the amino groups present in chitosan material is between 6.0 and 7.0, they can be protonated in very dilute acids or even close to neutral conditions, rendering a cationic nature to this biopolymer. This cationic nature is the basis of many of the benefits of the chitosan material. More generally, the cationic polysaccharides, like chitosan materials, can be considered as a linear polyelectrolyte with a high charge density which can interact with negatively charged surfaces, like proteins (e.g., by interfering with the negatively charged wall construction of microorganisms and/or enzymes, thereby acting as an antimicrobial agent and/or by reacting with the proteins present in bodily fluid, like menses, thereby acting as a gelifying agent for such fluid) or like anionic absorbent gelling materials that might be present in the articles herein as an optional ingredient (e.g., in a preferred embodiment of the present invention, thereby further enhancing the odor control properties of the cationic polysaccharides and providing outstanding absorption properties even in presence of electrolyte-containing solutions).

Preferred chitosan materials for use herein have an average degree of deacetylation (D.A.) of more than 75%, preferably from 80% to about 100%, even more preferably from 90% to 100% and most preferably from 95% to about 100%. The degree of deacetylation refers to the percentage of the amine groups that are deacetylated. This characteristic is directly related to the hydrogen bonding existing in this biopolymer, affecting its structure, solubility and ultimately its reactivity. The degree of deacetylation can be determined by titration, dye adsorption, UV-VIS, IR, and NMR spectroscopy.

The degree of deacetylation will influence the cationic properties of chitosan materials. By increasing the degree of deacetylation the cationic character of chitosan materials will increase and thus their antimicrobial properties, absorbing ability and gelifying ability.

Suitable chitosan materials to use herein include both water-soluble and water insoluble chitosan. As used herein, a material will be considered to be water-soluble when it substantially dissolves in excess water to form a clear and stable solution, thereby, losing its initially particulate form and becoming essentially molecularly dispersed throughout the water solution. Particularly suitable chitosan materials for use herein are water soluble, i.e., at least 0.5 gram, preferably at least 1 gram and most preferably at least 2 grams of the chitosan materials are soluble in 100 grams of water at 25° C. and one atmosphere. By "solubility" of a given compound it is to be understood herein the amount of said compound solubilised in de-ionized water at 25° C. and one atmosphere in absence of precipitate.

As a general rule, the water-soluble chitosan materials will be free from a substantial degree of crosslinking, as crosslinking tends to render the chitosan materials water insoluble.

Water-soluble chitosan materials as defined herein have the benefit to be more active in terms of odor control towards most of the malodorous compounds, present and soluble in the bodily fluid. Indeed such water-soluble chitosan materials have the ability to absorb and/or electrostatically interfere with water-soluble malodorous components like short chain acid (e.g., butyric acid) or low molecular weight alcohol (e.g., ethanol).

Chitosan materials (i.e., chitosan and -chitosan salts, modified chitosans and cross-linked chitosans) may generally have a wide range of molecular weights. Chitosan materials with a wide range of molecular weights are suitable for use in the present invention, typically chitosan materials for use herein have a molecular weight ranging from 1 000 to 10 000 000 grams per gram moles and more preferably from 2 000 to 1 000 000. Molecular weight means weight average molecular weight. Methods for determining the weight average molecular weight of chitosan materials are known to those skilled in the art. Typical methods include for example light scattering, intrinsic viscosity and gel permeation chromatography. It is generally most convenient to express the molecular weight of a chitosan material in terms of its viscosity in a 1.0 weight percent aqueous solution at 25° C. with a Brookfield viscometer. It is common to indirectly measure the viscosity of the chitosan material by measuring the viscosity of a corresponding chitosan salt, such as by using a 1.0 weight percent acetic acid aqueous solution. Chitosan materials suitable for use in the present invention will suitably have a viscosity in a 1.0 weight percent aqueous solution at 25° C. of from about 1 mPa·s (1 centipoise) to about 80,000 mPa·s (80,000 centipoise), more suitably from about 30 mPa·s (30 centipoise) to about 10,000 mPa·s (10,000 centipoise), even more suitably from 50 mPa·s (50 centipoise) to about 1,000 mPa·s (1,000 centipoise) and most suitably from 100 mPa·s (100 centipoise) to about 500 mPa·s (500 centipoise).

Chitosan materials pH depends on the preparation of the chitosan materials. Preferred chitosan materials for use herein have an acidic pH, typically in the range of 4 to 6, more preferably from 4 to 5.5 and even more preferably from 4.5 to 5.5. Highly preferred pH is around pH 5, which corresponds to the skin pH. By pH of chitosan material it is meant herein the pH of a 1% chitosan solution (1 gram of chitosan material dissolved in 100 grams of distilled water) measured by pH-meter.

The cationic properties of the chitosan materials and thus their antimicrobial, absorbing ability and gelifying ability increase with their acidic character. However too high acidity is detrimental to skin safety. Thus it is highly preferred herein to use chitosan materials with a pH in the range of 4.5 to 5.5, thereby delivering the best compromise between odor control and fluid handling properties on one side and skin compatibility on the other side.

Particularly suitable aminopolysaccharides for use herein include aminopolysaccharide salts, especially chitosan salts. A variety of acids can be used for forming aminopolysaccharide salts like chitosan salts. Suitable acids for use are soluble in water or partially soluble in water, are sufficiently acidic to form the ammonium salt of the aminopolysaccharide and yet not sufficiently acidic to cause hydrolysis of the aminopolysaccharide, and are present in amount sufficient to protonate the reactive sites of the deacetylated aminopolysaccharide.

Preferred acids can be represented by the formula:

R—(COOH)$_n$ wherein n has a value of 1 or 2 or 3 and R represents a mono- or divalent organic radical composed of carbon, hydrogen and optionally at least one of oxygen, nitrogen and sulfur or R is simply a hydroxyl group. Preferred acids are the mono- and dicarboxylic acids composed of carbon, hydrogen, oxygen and nitrogen (also called herein after amino acids). Such acids are highly desired herein as they are biologically acceptable for use against or in proximity to the human body. Illustrative acids, in addition to those previously mentioned include, among others, citric acid, formic acid, acetic acid, N-acetylglycine, acetylsalicylic acid, fumaric acid, glycolic acid, iminodiacetic acid, itaconic acid, lactic acid, maleic acid, malic acid, nicotinic acid, 2-pyrrolidone-5-carboxylic acid, salicylic acid, succinamic acid, succinic acid, ascorbic acid, aspartic acid, glutamic acid, glutaric acid, malonic acid, pyruvic acid, sulfonyldiacetic acid, benzoic acid, epoxysuccinic acid, adipic acid, thiodiacetic acid and thioglycolic acid. Any aminopolysaccharide salts, especially chitosan salts formed from the reaction of the aminopolysaccharide with any of these acids are suitable for use herein.

Examples of chitosan salts formed with an inorganic acid include, but are not limited to, chitosan hydrochloride, chitosan hydrobromide, chitosan phosphate, chitosan sulphonate, chitosan chlorosulphonate, chitosan chloroacetate and mixtures thereof. Examples of chitosan salts formed with an organic acid include, but are not limited to, chitosan formate, chitosan acetate, chitosan lactate, chitosan glycolate, chitosan malonate, chitosan epoxysuccinate, chitosan benzoate, chitosan adipate, chitosan citrate, chitosan salicylate, chitosan propionate, chitosan nitrilotriacetate, chitosan itaconate, chitosan hydroxyacetate, chitosan butyrate, chitosan isobutyrate, chitosan acrylate, and mixtures thereof. It is also suitable to form a chitosan salt using a mixture of acids including, for example, both inorganic and organic acids.

Preferred aminopolysaccharide salts, and especially chitosan salts for use herein are those formed by the reaction of aminopolysaccharides with an amino acid. Amino acids are molecules containing both an acidic and amino functional group. The use of amino acids is highly preferred as those aminopolysaccharide amino salts have higher skin compatibility. Indeed most of the amino acids are naturally present on the skin and thus are non-irritating. Chitosan salts of pyrrolidone carboxylic acid are effective moisturizing agents and are non-irritating to skin. Such chitosan materials are suitable in case of accidental low rewetting occurrence and/or misuse of the articles.

Amino acids for use herein include both linear and/or cyclo amino acids. Examples of amino acids for use herein include, but are not limited to, alanine, valine, leucine, isoleucine, prolinephenylalanine, triptofane, metionine, glycine, serine, cysteine, tyrosine, asparagine, glutamine, aspartic acid, glutamic acid, lysine, arginine, istydine, hydroxyproline and the like. A particularly suitable example of cyclo amino acid is pyrrolidone carboxylic acid, which is a carboxylic acid of pyrrolidin-2-one as per following formula:

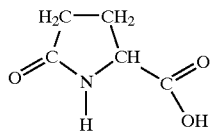

Highly preferred chitosan salts are chitosan pyroglutamate salt, which is a mixture of chitosan (a macromolecule) and pyroglutamic acid (independent monomers), chitosonium pyrrolidone carboxylate, which is the chitosan salt of 2-pyrrolidone-5-carboxylic acid.

Reference is made to WO 98/07618, which describes in details processes for the preparation of such aminopolysaccharide salts.

Other aminopolysaccharide materials suitable for use herein include cross-linked aminopolysaccharides and modified aminopolysaccharides, especially cross-linked chitosans and modified chitosans.

Suitable crosslinking agents for use herein are organic compounds having at least two functional groups or functionalities capable of reacting with active groups located on the aminopolysaccharide, typically chitosan materials. Examples of such active groups include, but are not limited to, carboxylic acid (—COOH), or hydroxyl (—OH) groups. Examples of such suitable crosslinking agents include, but are not limited to, diamines, polyamines, diols, polyols, dicarboxylic acids, polycarboxylic acids, aminocarboxylic acids, aminopolycarboxylic acids polyoxides and the like. One way to introduce a crosslinking agent with the chitosan solution is to mix the crosslinking agent with chitosan during preparation of the solution. Another suitable crosslinking agent comprises a metal ion with more than two positive charges, such as $Ca^{2+}$, $Al^{3+}$, $Fe^{3+}$, $Ce^{3+}$, $Ce^{4+}$, $Ti^{4+}$, $Zr^{4+}$, and $Cr^{3+}$. Since the cations on chitosan possess antimicrobial properties, it is preferred herein to not use a crosslinking agent reacting to the cations, unless no alternative crosslinking agent is available.

In the embodiment herein where crosslinking agents are used, a suitable amount of crosslinking agent is from 0.001 to 30 weight percent based on the total dry weight of chitosan used to prepare the crosslinked-chitosan, more specifically from 0.02 to 20 weight percent, more specifically from 0.05 to 10 weight percent and most preferably from 0.1 to 5 weight percent.

Modified chitosans or chitins for use herein are any chitosan or chitin where the glucan chains carry pendant groups. Examples of such modified chitosans include carboxymethyl chitosan, methyl pyrrolidinone chitosan, glycol chitosan and the like. Methyl pyrrolidone chitosan is for instance described in U.S. Pat. No. 5,378,472, incorporated herein by reference. Water-soluble glycol chitosan and carboxymethyl chitosan are for instance described in WO 87/07618, incorporated herein by reference Particularly suitable modified chitosans for use herein include water-soluble covalently bonded chitosan derivatives or ionically bonded chitosan derivatives obtained by contacting salt of chitosan with electrophilic organic reagents. Such water-soluble chitosan derivatives are described in EP-A737 692, which is herein incorporated by reference.

Suitable electrophilic organic reagents suitable for use for the preparation of chitosan derivatives contain from 2 to 18 carbon atoms or more per molecule and typically from 2 to 10 carbon atoms per molecule. In addition the electrophilic organic reagents contain groups, which are reactive, i.e. capable of forming a covalent bond with a nucleophile. Typical electrophilic organic reagents include, for example, ethylene oxide, propylene oxide, butylene oxide, glycidol, 3-chloro-1,2-propanediol, methyl chloride, ethyl chloride, isatoic anhydride, succinic anhydride, octenylsuccinic anhydride, acetic anhydride, gamma-butyrolactone, b-propiolactone, 1,3-propanesultone, acrylamide, glycidyltrimethyl ammonium chloride, glycidyldimethyl alkylammonium chloride such as lauryl, sodium chlorosulfonate, dimethyl sulfate, sodium chloroethanesulfonate, monochloroacetic acid, alkyl phenyl glycidyl ethers, glycidyl trimethoxysilanes, 1,2-epoxy dodecane. One preferred class of electrophilic organic reagent includes those electrophilic organic reagents, which contain an epoxide group, at least one acid group, preferably a diacid group and have from 3 to 18, preferably from 3 to 6 carbon atoms per molecule. Other preferred electrophilic organic reagents include cis-electrophilic organic reagents and trans-electrophilic organic reagent, with cis-electrophilic organic reagents being especially preferred. The electrophilic organic reagent may react with either the free amine or the underivatized hydroxyl groups of the chitosan. It is known that the amine functionality of the chitosan is generally regarded as a stronger nucleophilic site than the hydroxyl groups. Consequently weaker electrophiles will tend to react more readily with the amine groups than with the hydroxyl groups of the chitosan.

Preferably an effective amount of electrophilic organic reagent is substituted onto the chitosan to achieve the desired properties of the chitosan derivative, namely its water-soluble properties. Typically the chitosan derivatives suitable for use herein (modified chitosan) have a MS of from 0.03 to 10 moles of the electrophilic organic reagent per mole of glucosamine monomer unit. The term molar substitution (MS), means the moles of electrophilic organic reagent substituted on the chitosan per mole of glucosamine monomer unit.

In addition further modified chitosan can be prepared which contain other substituent groups, such as hydroxalkyl ether group (e.g., hydroxyethyl or hydroxypropyl ether groups), carboxyalkyl ether groups (e.g., carboxymethyl group), amide groups (e.g., succinyl groups), ester groups (e.g., acetate groups) or amino groups (e.g., 3-(trimethylammonium chloride)-2-hydroxylpropyl or 3-(dimethyloctadecylammonium chloride)-2-hydroxpropyl ether groups) in addition to the electrophilic organic reagent groups. These other substituent groups may be introduced prior to or subsequent to the reaction with the electrophilic organic reagent, or introduced simultaneously by reaction of the chitosan salt with the electrophilic organic reagent and the other derivatizing reagent.

Typically such covalently bonded chitosan derivative might be obtainable by a process which includes the step of (a) dispersing a salt of chitosan (e.g., any one of those described herein before) in an effective amount of an aqueous caustic medium to form a neutralized chitosan containing free amine groups, (b) introducing an electrophilic organic reagent in the slurry and (c) maintaining the slurry at a temperature and time effective to promote the substitution of the electrophilic organic reagent onto the chitosan to form a covalently bonded chitosan derivative and the dissolution of the covalently bonded chitosan into the aqueous medium. The chitosan derivatives can be prepared in either salt form, i.e., ionically bonded, or in the covalently bonded form. Processes for the preparation of such chitosan derivatives are described in depth in EP-A-737 692, incorporated herein by reference.

Suitable chitosans are commercially available from numerous vendors. Exemplary of a commercially available chitosan materials are those available from for example the Vanson Company. The preferred chitosan salt for use herein is chitosan pyrrolidone carboxylate (also called chitosonium pyrrolidone carboxylate), which has a degree of deacetylation more than 85%, a water solubility of 1% (1 gram is soluble in 100 grams of distilled water at 25° C. and one atmosphere), a pH of 4.5 and a viscosity between 100–300 cps. Chitosan pyrrolidone carboxylate is commercially available under the name Kytamer® PC from Amerchol Corporation.

Typically, the articles like disposable absorbent articles comprise the cationic polysaccharide or a mixture thereof at a level of from 0.5 $gm^{-2}$ to 500 $gm^{-2}$, preferably from 1 to 200 $gm^{-2}$, more preferably from 3 $gm^{-2}$ to 100 $gm^{-2}$ and most preferably from 4 $gm^{-2}$ to 50 $gm^{-2}$ The Odor Controlling Agents The articles according to the present invention further comprise on top of the cationic polysaccharide or mixture thereof described herein before, at least one additional odor-controlling agent or a mixture thereof.

Typically, the articles like disposable absorbent articles herein comprise from 1 to 600 $gm^{-2}$, more preferably from 5 to 400 $gm^{-2}$, most preferably from 10 to 200 $gm^{-2}$, of the odor controlling agent or a mixture thereof.

Suitable odor controlling agents for use herein include odor absorbent agents known to those skilled in the art, namely activated carbons, clays, zeolites, kieselguhr, diatomaceous earth, starches, cyclodextrin, ion exchange resins and the like. Preferred herein are zeolites and/or cyclodextrin. Other suitable odor controlling agents for use herein include chelating agents or a mixture thereof. The articles herein may contain mixtures of odor absorbent agents with chelating agents.

The present invention is based on the finding that the cationic polysaccharides, especially chitosan materials, together with an odor controlling agent, preferably an odor absorbent agent (preferably zeolite and/or cyclodextrin) and/or a chelating agent (preferably ethylene diamine tetra acetates) deliver a synergistic odor control benefit towards malodors associated with bodily fluids, especially menses.

It is speculated that the cationic polysaccharides herein prevent the formation of malodorous compounds, typically by reducing or even inhibiting the microbial and enzymatic development in bodily fluid, thereby reducing the total amount of malodorous compounds associated with bodily fluid. This results in more effective use of odor absorbent agents over prolonged period of time before the saturation of the active center of absorption of such agents. Advantageously these odor absorbent agents, like zeolite or cyclodextrine or derivatives thereof, control odor associated with bodily fluids/exudates not only by absorbing malodorous components present in the bodily fluids coming into contact therewith, typically in the absorbent article, but also by absorbing the volatile malodorous components present in the headspace of the absorbent article which would otherwise not have been controlled in presence of the cationic polysaccharides used alone as the sole odor controlling agent in the absorbent article.

In a preferred embodiment herein the cationic polysaccharide and the odor absorbent agent are present in weight ratio from the cationic polysaccharide to the odor absorbent agent of from 1:10 to 10:1, preferably from 1:5 to 5:1 and more preferably at a ratio around 1:1. Indeed it is within these ratios ranges that optimum odor control properties are obtained versus bodily fluids.

Zeolite

A particularly suitable odor absorbent agent herein is zeolite. The use and manufacture of zeolite material is well know in the literature and is described in the following reference texts: ZEOLITE SYNTHESIS, ACS Symposium Series 398, Eds. M. L. Occelli and H. E Robson (1989) pages 2–7; ZEOLITE MOLECULAR SIEVES, Structure, Chemistry and Use, by D. W. Breck, John Wiley and Sons (1974) pages 245–250, 313–314 and 348–352; MODERN APPLICATIONS OF MOLECULAR SIEVE ZEOLITES, Ph.D. Dissertation of S. M. Kuznicki, U. of Utah (1980), available from University of Microfilms International, Ann Arbor, Mich., pages 2–8.

Zeolites are crystalline aluminosilicates of group IA and group IIA elements such as Na, K, Mg, and Ca are chemically represented by the empirical formula:

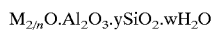

where y is 2 or greater, n is the cation valence, and w is the water content in the voids of the zeolite.

Structurally, zeolites are complex, crystalline inorganic polymers based on an infinitely extending framework of $AlO_4$ and $SiO_4$ tetrahedra linked to each other by sharing of oxygen ions. This framework structure contains channels or interconnected voids that are occupied by the cations and water molecules.

The structural formula of a zeolite is based on the crystal unit cell, the smallest unit of structure, represented by

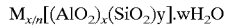

where n is the valence of cation M, w is the number of water molecules per unit cell, x and y are the total number of tetrahedra per unit cell, y/x usually having values of 1–5.

Zeolites may be naturally derived or synthetically manufactured. The synthetic zeolites being preferred for use herein. Suitable zeolites for use herein include zeolite A, zeolite P, zeolite Y, zeolite X, zeolite DAY, zeolite ZSM-5, or mixtures thereof. Most preferred is zeolite A.

According to the present invention the zeolite is preferably hydrophobic. This is typically achieved by increasing the molar ratio of the $SiO_2$ to $AlO_2$ content such that the ratio of x to y is at least 1, preferably from 1 to 500, most preferably from 1 to 6.

According to the present invention the articles typically comprise from 0 to 300 $gm^{-2}$, more preferably from 40 to 250 $gm^{-2}$ most preferably from 60 to 200 $gm^{-2}$, of zeolite based on 100% purity or a mixture thereof.

Cyclodextrin and Derivatives Thereof

A particularly suitable odor absorbent agent for use herein is cyclodextrin or a derivative thereof or a mixture thereof. These materials are preferred herein due to their dual function of solubilising cationic polysaccharides, typically those that are partly water soluble or non water-soluble and of their own ability to absorb odor.

Cyclodextrin or a derivative thereof may thus act as a carrier for the cationic polysaccharides, typically chitosan materials, and thus contribute to bring chitosan materials, especially those being partly water soluble or non soluble (i.e., typically having a solubility in water of less than 0.5 gram per 100 grams of distilled water at 25° C. and one atmosphere), into closer contact with the liquid bodily fluid and thus the water soluble malodorous components resulting from the degradation of lipids, proteins and/or sugars like amine, butyric acid and the like. It is speculated that cyclodextrin or derivatives thereof help to further solubilise the cationic polysaccharides and this results in significantly improved overall odor control (synergistic effect).

The unique shape and physical-chemical property of the cavity enable the cyclodextrin molecules to absorb (form inclusion complexes with) organic molecules or parts of organic molecules, which can fit into the cavity.

As used herein, the term "cyclodextrin" includes any of the known cyclodextrins such as unsubstituted cyclodextrins containing from six to twelve glucose units, especially, alpha-cyclodextrin, beta-cyclodextrin, gamma-cyclodextrin and/or their derivatives and/or mixtures thereof. The alpha-cyclodextrin consists of six glucose units, the beta-cyclodextrin consists of seven glucose units, and the gamma-cyclodextrin consists of eight glucose units arranged in a donut-shaped ring. The specific coupling and conformation of the glucose units give the cyclodextrins a rigid, conical molecular structure with a hollow interior of a specific volume. The "lining" of the internal cavity is formed by hydrogen atoms and glycosidic bridging oxygen atoms; therefore this surface is fairly hydrophobic. Non-derivatised (normal) beta-cyclodextrin can be used herein.

Particularly preferred cyclodextrins useful in the present invention are highly water-soluble such as, alpha-cyclodextrin and derivatives thereof, gamma-cyclodextrin and derivatives thereof, derivatised beta-cyclodextrins, and/or mixtures thereof.

The derivatives of cyclodextrin consist mainly of molecules wherein some of the OH groups are converted to OR groups. Cyclodextrin derivatives include, e.g., those with short chain alkyl groups such as methylated cyclodextrins, and ethylated cyclodextrins, wherein R is a methyl or an ethyl group; those with hydroxyalkyl substituted groups, such as hydroxypropyl cyclodextrins and/or hydroxyethyl cyclodextrins, wherein R is a —CH$_2$—CH(OH)—CH$_3$ or a —CH$_2$CH$_2$—OH group; branched cyclodextrins such as maltose-bonded cyclodextrins; cationic cyclodextrins such as those containing 2-hydroxy-3(dimethylamino)propyl ether, wherein R is CH$_2$—CH(OH)—CH$_2$—N(CH$_3$)$_2$ which is cationic at low pH; quaternary ammonium, e.g., 2-hydroxy-3-(trimethylammonio)propyl ether chloride groups, wherein R is CH$_2$—CH(OH)—CH$_2$—N$^+$(CH$_3$)$_3$ Cl$^-$; anionic cyclodextrins such as carboxymethyl cyclodextrins, cyclodextrin sulfates, and cyclodextrin succinylates; amphoteric cyclodextrins such as carboxymethyl/quaternary ammonium cyclodextrins; cyclodextrins wherein at least one glucopyranose unit has a 3-6-anhydro-cyclomalto structure, e.g., the mono-3-6-anhydrocyclodextrins, as disclosed in "Optimal Performances with Minimal Chemical Modification of Cyclodextrins", F. Diedaini-Pilard and B. Perly, The 7th International Cyclodextrin Symposium Abstracts, April 1994, p. 49, herein incorporated by reference; and mixtures thereof. Other cyclodextrin derivatives are disclosed in U.S. Pat. No. 3,426,011, Parmerter et al., issued Feb. 4, 1969; U.S. Pat. Nos. 3,453,257; 3,453,258; 3,453,259; and 3,453,260, all in the names of Parmerter et al., and all issued Jul. 1, 1969; U.S Pat. No. 3,459,731, Gramera et al., issued Aug. 5, 1969; U.S. Pat. No. 3,553,191, Parmerter et al., issued Jan. 5, 1971; U.S. Pat. No. 3,565,887, Parmerter et al., issued Feb. 23, 1971; U.S. Pat. No. 4,535,152, Szejtli et al., issued Aug. 13, 1985; U.S. Pat. No. 4,616,008, Hirai et al., issued Oct. 7, 1986; U.S. Pat. No. 4,678,598, Ogino et al., issued Jul. 7, 1987; U.S. Pat. No. 4,638,058, Brandt et al., issued Jan. 20, 1987; and U.S. Pat. No. 4,746,734, Tsuchiyama et al., issued May 24, 1988; all of said patents being incorporated herein by reference.

Highly water-soluble cyclodextrins are those having water solubility of at least about 10 g in 100 ml of water at room temperature, preferably at least about 20 g in 100 ml of water, more preferably at least about 25 g in 100 ml of water at room temperature. These are easy to use, but are typically more expensive than the non-derivatised beta-cyclodextrin. Examples of preferred water-soluble cyclodextrin derivatives suitable for use herein are hydroxypropyl alpha-cyclodextrin, methylated alpha-cyclodextrin, methylated beta-cyclodextrin, hydroxyethyl beta-cyclodextrin, and hydroxypropyl beta-cyclodextrin. Hydroxyalkyl cyclodextrin derivatives preferably have a degree of substitution of from about 1 to about 14, more preferably from about 1.5 to about 7, wherein the total number of OR groups per cyclodextrin is defined as the degree of substitution. Methylated cyclodextrin derivatives typically have a degree of substitution of from about 1 to about 18, preferably from about 3 to about 16. A known methylated beta-cyclodextrin is heptakis-2,6-di-O-methyl-β-cyclodextrin, commonly known as DIMEB, in which each glucose unit has about 2 methyl groups with a degree of substitution of about 14. A preferred, more commercially available methylated beta-cyclodextrin is a randomly methylated beta-cyclodextrin having a degree of substitution of about 12.6. The preferred cyclodextrins are available, e.g., from Cerestar USA, Inc. and Wacker Chemicals (USA), Inc.

It can be desirable to use a mixture of cyclodextrins. Such mixtures can complex with a wider range of odor molecules having a wider range of molecular sizes. Preferably at least a portion of such a mixture of cyclodextrins is alpha-cyclodextrin or its derivatives, gamma-cyclodextrin or its derivatives thereof, and/or beta-cyclodextrin or its derivatives.

According to the present invention the articles typically comprise from 0 to 300 gm$^{-2}$, more preferably from 5 to 250 gm$^{-2}$ most preferably from 7 to 200 gm$^{-2}$, of cyclodextrin or derivative thereof or mixture thereof.

Chelating Agents

Suitable chelating agents for use herein are those known to those skilled in the art. Suitable chelating agents include for example phosphonate chelating agents, polyfunctionally-substituted aromatic chelating agents, amino carboxylate chelating agents, other chelating agents like ethylene diamine N,N'-disuccinic acid, aspartic acid, glutamic acid, malonic acid, glycine and mixtures thereof.

Suitable phosphonate chelating agents to be used herein may include ethydronic acid, alkali metal ethane 1-hydroxy diphosphonates as well as amino phosphonate compounds, including amino alkylene poly (alkylene phosphonate), alkali metal ethane 1-hydroxy diphosphonates, nitrilo trimethylene phosphonates, ethylene diamine tetra methylene phosphonates, aminotri(methylene phosphonates) (ATMP) and diethylene triamine penta methylene phosphonates. The phosphonate compounds may be present either in their acid form or as salts of different cations on some or all of their acid functionalities. Typically, these amino phosphonates do not contain alkyl or alkenyl groups with more than 6 carbon atoms. Preferred phosphonate chelating agents to be used herein are diethylene triamine penta methylene phosphonates (DETPMP). Such phosphonate chelating agents are commercially available from Monsanto under the trade name DEQUEST®.

Polyfunctionally-substituted aromatic chelating agents may also be useful in the compositions herein. See U.S. Pat. No. 3,812,044, issued May 21, 1974, to Connor et al. Preferred compounds of this type in acid form are dihydroxydisulfobenzenes such as 1,2-dihydroxy-3,5-disulfobenzene.

A preferred biodegradable chelating agent for use herein is ethylene diamine N,N'-disuccinic acid, or alkali metal, or alkaline earth, ammonium or substitutes ammonium salts thereof or mixtures thereof. Ethylenediamine N,N'-disuccinic acids, especially the (S,S) isomer have been extensively described in U.S. Pat. No. 4,704,233, Nov. 3, 1987. to Hartman and Perkins. Ethylenediamine N,N'-disuccinic acids is, for instance, commercially available under the trade name ssEDDS® from Palmer Research Laboratories.

Suitable amino carboxylate chelating agents to be used herein include ethylene diamine tetra acetates (EDTA), diethylene triamine pentaacetates, diethylene triamine pentaacetate (DTPA), N-hydroxyethylethylenediamine triacetates, nitrilotri-acetates, ethylenediamine tetrapropionates, triethylenetetraaminehexa-acetates, diethylenetriamine pentaacetates, ethanol-diglycines, propylene diamine tetracetic acid (PDTA) and methyl glycine di-acetic acid (MGDA), both in their acid form, or in their alkali metal, ammonium, and substituted ammonium salt forms. Particularly suitable amino carboxylates to be used herein are ethylene diamine tetra acetates (EDTA), diethylene triamine penta acetic acid (DTPA) or mixture thereof.

The more preferred chelating agents for use herein are selected from ethylenediamine tetracetate, -triacetate, -diacetate, and -monoacetate, ethylenediamine N,N,-disuccinic acid (sodium salt), ethylenediamine penta (methylene phosphonic acid) (sodium salt), ethylenediamine tetra (methylene phosphonic acid) or mixtures thereof. Most preferably the chelating agent is ethylene diamine tetracetate.

According to the present invention the articles typically comprise from 0 to 300 $gm^{-2}$, more preferably from 5 to 250 $gm^{-2}$ most preferably from 7 to 200 $gm^{-2}$, of chelating agent or mixture thereof.

It is speculated that the chelating agents herein participate to the antimicrobial activities of the cationic polysaccharides herein. Indeed they chelate positively charged nutriments for microorganisms like growth factors (e.g., calcium, magnesium and/or potassium) that are vital for any microbial development, thereby reducing such development. They thus supplement the antimicrobial direct activity of the cationic polysaccharides herein, especially chitosan materials. This is even more the case in the preferred embodiments of the present invention, where chitosan materials with high degree of deacetylation are used (more than 75%) as defined herein, and where as a consequence such chitosan materials are not able to act as chelating agents towards positively charged nutriments.

In a preferred embodiment herein the cationic polysaccharide and the chelating agent are present in weight ratio from the cationic polysaccharide to the chelating agent of from 1:10 to 10:1, preferably from 1:5 to 5:1 and more preferably from 1:3 to 3:1. Indeed it is within these ratios ranges that optimum odor control properties are obtained versus bodily fluids.

Optional Agents

The articles according to the present invention may further comprise other conventional agents like absorbent gelling materials.

Absorbent Gelling Materials

As is well known from recent commercial practice, absorbent gelling materials (sometimes referred to as "supersorbers") are becoming broadly used in absorbent articles. AGMs are materials, which have the twofold property of absorbing and retaining fluids and odors, and thus further contribute to the benefit of the present invention.

Particularly preferred absorbent gelling materials for use herein are anionic absorbent gelling materials, i.e., absorbent gelling materials that are predominantly negatively charged. These absorbent gelling materials can be any material having superabsorbent properties in which the functional groups are anionic, namely sulphonic groups, sulphate groups, phosphate groups or carboxyl groups. Preferably the functional groups are carboxyl groups. Particularly preferred anionic absorbent gelling materials for use herein are synthetic anionic absorbent gelling materials. Synthetic anionic absorbent gelling materials are preferred herein as they deliver higher odor and fluid absorption performance, this even under pressure, as compared to the absorption performance associated with natural anionic absorbent gelling materials like anionic polysaccharides when used in the same absorbent article.

Generally the functional groups are attached to a slightly cross-linked acrylic base polymer. For example the base polymer may be a polyacrylamide, polyvinyl alcohol, ethylene maleic anhydride copolymer, polyvinylether, polyvinyl sulphonic acid, polyacrylic acid, polyvinylpyrrolidone and polyvinylmorpholine. Copolymers of these monomers can also be used. Particular base polymers include cross-linked polyacrylates, hydrolyzed acrylonitrile grafted starch, starch polyacrylates and isobutylene maleic anhydride copolymers.

Such materials form hydrogels on contact with water (e.g., with urine, blood, and the like). One highly preferred type of hydrogel-forming, absorbent gelling material is based on polyacids, especially polyacrylic acid. Hydrogel-forming polymeric materials of this type are those, which, upon contact with fluids (i.e., liquids) such as water or body fluids, imbibe such fluids and thereby form hydrogels. These preferred absorbent gelling materials will generally comprise substantially water-insoluble, slightly cross-linked, partially neutralized, hydrogel-forming polymer materials prepared from polymerisable, unsaturated, acid-containing monomers. In such materials, the polymeric component formed from unsaturated, acid-containing monomers may comprise the entire gelling agent or may be grafted onto other types of polymer moieties such as starch or cellulose. Acrylic acid grafted starch materials are of this latter type. Thus, the preferred absorbent gelling materials include hydrolyzed acrylonitrile grafted starch, acrylic acid grafted starch, polyacrylates, maleic anhydride-based copolymers and combinations thereof. Especially preferred absorbent gelling materials are the polyacrylates and acrylic acid grafted starch.

Whatever the nature of the polymer components of the preferred absorbent gelling materials, such materials will in general be slightly cross-linked. Crosslinking serves to render these preferred hydrogel-forming absorbent materials substantially water-insoluble, and cross-linking also in part determines the gel volume and extractable polymer characteristics of the hydrogels formed there from. Suitable cross-linking agents are well known in the art and include, for example, (1) compounds having at least two polymerisable double bonds; (2) compounds having at least one polymerisable double bond and at least one functional group reactive with the acid-containing monomer material; (3) compounds having at least two functional groups reactive with the acid-containing monomer materials; and (4) polyvalent metal compounds which can from ionic cross-linkages. Cross-linking agents of the foregoing types are described in greater detail in Masuda et al; U.S. Pat. No. 4,076,663; Issued Feb. 28, 1978. Preferred cross-linking agents are the di- or polyesters of unsaturated mono-or polycarboxylic acids with polyols, the bisacrylamides and the di-or triallyl amines. Especially preferred cross-linking agents are N,N'-methylenebisacrylamide, trimethylol propane triacrylate and triallyl amine. The cross-linking agent will generally comprise from about 0.001 mole percent to 5 mole percent of the preferred materials. More preferably, the cross-linking agent will comprise from about 0.01 mole percent to 3 mole percent of the gelling materials used herein.

The preferred absorbent gelling materials used herein are those which have a relatively high capacity for imbibing fluids encountered in the absorbent articles; this capacity can be quantified by referencing the "gel volume" of said absorbent gelling materials. Gel volume can be defined in terms of the amount of synthetic urine absorbed by any given absorbent gelling agent buffer and is specified as grams of synthetic urine per gram of gelling agent.

Gel volume in synthetic urine (see Brandt, et al, below) can be determined by forming a suspension of about 0.1–0.2 parts of dried absorbent gelling material to be tested with about 20 parts of synthetic urine. This suspension is maintained at ambient temperature under gentle stirring for about 1 hour so that swelling equilibrium is attained. The gel volume (grams of synthetic urine per gram of absorbent gelling material) is then calculated from the weight fraction of the gelling agent in the suspension and the ratio of the liquid volume excluded from the formed hydrogel to the total volume of the suspension. The preferred absorbent gelling materials useful in this invention will have a gel volume of from about 20 to 70 grams, more preferably from about 30 to 60 grams, of synthetic urine per gram of absorbent gelling material.

Another feature of the most highly preferred absorbent gelling materials relates to the level of extractable polymer material present in said materials. Extractable polymer levels can be determined by contacting a sample of preferred absorbent gelling material with a synthetic urine solution for the substantial period of time (e.g., at least 16 hours) which is needed to reach extraction equilibrium, by then filtering the formed hydrogel from the supernatant liquid, and finally by then determining the polymer content of the filtrate. The particular procedure used to determine extractable polymer content of the preferred absorbent gelling agent buffers herein is set forth in Brandt, Goldman and Inglin; U.S. Pat. No. 4,654,039; Issues Mar. 31, 1987, Reissue 32,649, The absorbent gelling materials which are especially useful in the absorbent articles herein are those which have an equilibrium extractable content in synthetic urine of no more than about 17%, preferably no more than about 10% by weight of the absorbent gelling material.

The preferred, slightly cross-linked, hydrogel-forming absorbent gelling materials will generally be employed in their partially neutralized form. For purposes described herein, such materials are considered partially neutralized when at least 25 mole percent, and preferably at least 50 mole percent of monomers used to form the polymer are acid group-containing monomers, which have been neutralized with a salt-forming cation. Suitable salt-forming cations include alkali metal, ammonium, substituted ammonium and amines. This percentage of the total monomers utilized, which are neutralized acid group-containing monomers, is referred to as the "degree of neutralization". Typically, commercial absorbent gelling materials have a degree of neutralization somewhat from 25% to 90%.

The absorbent gelling materials herein before described are typically used in the form of discrete particles. Such absorbent gelling materials can be of any desired shape, e.g., spherical or semi-spherical, cubic, rod-like polyhedral, etc. Shapes having a large greatest dimension/smallest dimension ratio, like needles and flakes, are also contemplated for use herein. Agglomerates of absorbent gelling material particles may also be used.

The size of the absorbent gelling material particles may vary over a wide range. For reason of industrial hygiene, average particle sizes smaller than about 30 microns are less desirable. Particles having a smallest dimension larger than about 2 mm may also cause a feeling of grittiness in the absorbent article, which is undesirable from a consumer aesthetics standpoint. Furthermore, rate of fluid absorption can be affected by particle size. Larger particles have very much reduced rates of absorption. Preferred for use herein are absorbent gelling material s particles substantially all of which have a particle size of from about 30 microns to about 2 mm. "Particle Size" as used herein means the weighted average of the smallest dimension of the individual particles.

The amount of absorbent gelling material particles used in the article according to the present invention, especially disposable absorbent articles, will typically range from 5 $gm^{-2}$ to 250 $gm^{-2}$, preferably from 7 $gm^{-2}$ to 150 $gm^{-2}$, more preferably from 10 $gm^{-2}$ to 100 $gm^{-2}$.

Anionic absorbent gelling materials are suitably used on top of the cationic polysaccharides and odor controlling agents herein as they further contribute to enhance the benefices of the present invention. Indeed the anionic absorbent gelling materials enhance the cationic properties of the cationic polysaccharides, thus their odor control properties. Without to be bound by any theory, it is believed that the negatively charged anionic groups of the anionic absorbent gelling materials protonate the cationic polysaccharides, thereby enhancing the cationic properties of for example chitosan materials.

Advantageously the addition of anionic absorbent gelling materials, namely synthetic anionic absorbent gelling materials as described herein (typically having a degree of neutralization of from 25% to 90%) on top of cationic polysaccharides, especially chitosan materials, in an absorbent article results in outstanding fluid absorption capacity not only towards water but especially towards electrolytes-containing solutions like menses.

Furthermore the use of anionic absorbent gelling materials, namely synthetic anionic absorbent gelling materials as described herein (typically having a degree of neutralization of from 25% to 90%) on top of cationic polysaccharides, especially chitosan materials, in an absorbent article, exhibit high gel strength during fluid absorption. Indeed this combination results in improved absorption capacity under load conditions, in decreased rewetting and wetting through and hence improved comfort.

Advantageously the presence of anionic synthetic absorbent gelling agents on top of the odor control system of the present invention results in optimum fluid absorption and optimum odor control of malodors typically associated with bodily fluids.

The Disposable Absorbent Article

The odor control system (i.e., at least a cationic polysaccharide and an odor controlling agent) as well as the optional absorbent gelling material may be incorporated into the absorbent article by any of the methods disclosed in the art, for example layered on the core of the absorbent article or mixed within the fibers of the absorbent core.

The cationic polysaccharide and the odor-controlling agent are preferably incorporated between two layers of cellulose tissue. Optionally the system may be bonded between two cellulose tissue layers with, for example, a hot melt adhesive or any suitable bonding system, as described in WO 94/01069.

In one embodiment of the present invention the cationic polysaccharide and the odor controlling agent are incorporated in a layered structure in accordance with the disclosure of WO 94/01069 or Italian patent application number TO 93A 001028. TO 93A 001028 describes a layered structure substantially as described in WO 94/01069 with the exception that TO 93A 001028 comprises a much higher quantity of absorbent gelling material in the intermediate layer which is between the fibrous layers (120 $gm^{-2}$) that would be incorporated as an optional component in the present invention. The intermediate layer comprises in particular a polyethylene powder as thermoplastic material, which is mixed with the odor controlling agent and cationic polysaccharide. The mixture is then heated such that the polyethylene melts and glues the laminate layers together. Adhesive lines are preferably also placed on the edges of the laminate to ensure that the edges of the laminate stick and any loose cationic polysaccharide powder and odor controlling agent powder present do not fall out of the laminate.

Alternatively, the polyethylene powder may be replaced by a conventional glue for instance those commercially available from ATO Findley under the name H20–31® to glue the laminate layers and/or components together. Advantageously this method step allows to avoid the heating step necessary when using polyethylene powder.

The cationic polysaccharide and the odor controlling agent may be distributed homogeneously or non homogeneously over the entire absorbent article or in at least one layer of the topsheet, or at least one layer of the backsheet or in at least one layer of the core or any mixture thereof. The cationic polysaccharide and the odor controlling agent may be distributed homogeneously or non homogeneously on the whole surface of the desired layer or layers, or on one or several area of the surface layer/layers to which it is positioned (e.g. central area and/or surrounding area like the edges of a layer of the absorbent article) or mixtures thereof.

The cationic polysaccharide and the odor-controlling agent may be positioned together in the same location (e.g., layer) or separately in different locations/layers. For example in one embodiment herein the odor controlling agent (e.g., zeolite and/or cyclodextrin and/or EDTA) is positioned such that at least a portion of the fluid/exudate comes into contact with it before the cationic polysaccharide, preferably chitosan material. Preferably the odor controlling agent is located in the core towards the topsheet or located in the topsheet itself (preferably the secondary topsheet) and the cationic polysaccharide is located further away from the topsheet than the odor controlling agent. In one embodiment of the present invention, the odor-controlling agent is positioned in at least one of the topsheet layers and the cationic polysaccharide, typically chitosan material, is positioned in the core. In another embodiment herein the odor controlling agent and the cationic polysaccharide are both located in the core, but the cationic polysaccharide is located beneath the odor-controlling agent, typically the cationic polysaccharide is located towards the backsheet. In another embodiment the odor controlling agent is located in the absorbent core and the cationic polysaccharide in the backsheet itself (preferably the secondary backsheet).

In a preferred embodiment herein, wherein an absorbent gelling material is present, the absorbent gelling material and the odor controlling agent are positioned such that at least a portion of the bodily fluid/exudate comes into contact with said absorbent gelling material and odor controlling agent before the cationic polysaccharide. In a highly preferred embodiment herein the absorbent gelling material and odor controlling agent are located in the absorbent core and the cationic polysaccharide, typically chitosan material, is located too in the absorbent core but further away from the topsheet than the absorbent gelling material and odor controlling agent. In an execution wherein the core is made of laminate of two layers of cellulose tissue, the absorbent gelling material and the odor controlling agent are incorporated between these two layers and the polysaccharide is applied on the layer positioned in proximity to the backsheet, preferably on the inner side of this layer so as to be in close proximity to the absorbent gelling material and odor controlling agent. Such executions are particularly beneficial for combining optimum odor control properties with optimum fluid handling, i.e., optimum odor and fluid absorption and retention without any leakage through or rewetting occurrence. The cationic properties of the cationic polysaccharides will be boosted due to the close proximity to the absorbent gelling material. Furthermore the cationic polysaccharide due to its gelifying properties will have the tendency to form a so-called impermeable layer towards the backsheet thereby preventing any leakage through.

The cationic polysaccharides and odor controlling agents as well as the optional absorbent gelling material if present may be incorporated as a powder, a granulate or can be sprayed in the form of for example a polysaccharide-containing solution and/or odor controlling agent-containing solution within the absorbent article. When used in a granulate or particulate form the cationic polysaccharides (e.g., chitosan material) and odor controlling agents as well as the optional absorbent gelling materials may be granulated separately and then mixed together or granulated together.

Typical disposable absorbent articles according to the preferred embodiments of the present invention are those as described herein after:

Absorbent Core

According to the present invention, the absorbent can include the following components: (a) an optional primary fluid distribution layer preferably together with a secondary optional fluid distribution layer; (b) a fluid storage layer; (c) an optional fibrous ("dusting") layer underlying the storage layer; and (d) other optional components. According to the present invention the absorbent may have any thickness depending on the end use envisioned.

a Primary/Secondary Fluid Distribution Layer

One optional component of the absorbent according to the present invention is a primary fluid distribution layer and a secondary fluid distribution layer. The primary distribution layer typically underlies the topsheet and is in fluid communication therewith. The topsheet transfers the acquired fluid to this primary distribution layer for ultimate distribution to the storage layer. This transfer of fluid through the primary distribution layer occurs not only in the thickness, but also along the length and width directions of the absorbent product. The also optional but preferred secondary distribution layer typically underlies the primary distribution layer and is in fluid communication therewith. The purpose of this secondary distribution layer is to readily acquire fluid from the primary distribution layer and transfer it rapidly to the underlying storage layer. This helps the fluid capacity of the underlying storage layer to be fully utilized. The fluid distribution layers can be comprised of any material typical for such distribution layers. In particular fibrous layers maintain the capillaries between fibers even when wet are useful as distribution layers.

b Fluid Storage Layer

Positioned in fluid communication with, and typically underlying the primary or secondary distribution layers, is a fluid storage layer. The fluid storage layer can comprise the cationic polysaccharides and optional absorbent gelling material. It preferably comprises the cationic polysaccharides and optional absorbent gelling materials in combination with suitable carriers.

Suitable carriers include materials, which are conventionally utilized in absorbent structures such as natural, modified or synthetic fibers, particularly modified or non-modified cellulose fibers, in the form of fluff and/or tissues. Most preferred are tissue or tissue laminates in the context of sanitary napkins and panty liners.

An embodiment of the absorbent structure made according to the present invention may comprise multiple layers comprises a double layer tissue laminate formed by folding the tissue onto itself. These layers can be joined to each other for example by adhesive or by mechanical interlocking or by hydrogen bridge bands. The cationic polysaccharides (together with the odor controlling agents) and optional absorbent gelling materials can be comprised between the layers.

Modified cellulose fibers such as the stiffened cellulose fibers can also be used. Synthetic fibers can also be used and include those made of cellulose acetate, polyvinyl fluoride, polyvinylidene chloride, acrylics (such as Orlon), polyvinyl acetate, non-soluble polyvinyl alcohol, polyethylene, polypropylene, polyamides (such as nylon), polyesters, bicomponent fibers, tricomponent fibers, mixtures thereof and the like. Preferably, the fiber surfaces are hydrophilic or are treated to be hydrophilic. The storage layer can also include filler materials, such as Perlite, diatomaceous earth, Vermiculite, etc., to improve liquid retention.

If the cationic polysaccharides and optional absorbent gelling materials are dispersed non-homogeneously in a carrier, the storage layer can nevertheless be locally homogenous, i.e. have a distribution gradient in one or several directions within the dimensions of the storage layer. Non-homogeneous distribution can also refer to laminates of carriers enclosing cationic polysaccharides and optional absorbent gelling materials partially or fully.

c Optional Fibrous ("Dusting") Layer

An optional component for inclusion in the absorbent core according to the present invention is a fibrous layer adjacent to, and typically underlying the storage layer. This underlying fibrous layer is typically referred to as a "dusting" layer since it provides a substrate on which to deposit absorbent gelling material in the storage layer during manufacture of the absorbent core. Indeed, in those instances where the absorbent gelling material is in the form of macro structures such as fibers, sheets or strips, this fibrous "dusting" layer need not be included. However, this "dusting" layer provides some additional fluid-handling capabilities such as rapid wicking of fluid along the length of the pad.

d Other Optional Components of the absorbent structure

The absorbent core according to the present invention can include other optional components normally present in absorbent webs. For example, a reinforcing scrim can be positioned within the respective layers, or between the respective layers, of the absorbent core. Such reinforcing scrims should be of such configuration as to not form interfacial barriers to fluid transfer. Given the structural integrity that usually occurs as a result of thermal bonding, reinforcing scrims are usually not required for thermally bonded absorbent structures.

The Topsheet

According to the present invention the absorbent article comprises as an essential component a topsheet. The topsheet may comprise a single layer or a multiplicity of layers. In a preferred embodiment the topsheet comprises a first layer, which provides the user-facing surface of the topsheet and a second layer (also called secondary topsheet) between the first layer and the absorbent structure/core.

The topsheet as a whole and hence each layer individually needs to be compliant, soft feeling, and non-irritating to the wearer's skin. It also can have elastic characteristics allowing it to be stretched in one or two directions. According to the present invention the topsheet may be formed from any of the materials available for this purpose and known in the art, such as woven and non-woven fabrics and films.

In a preferred embodiment of the present invention at least one of the layers, preferably the upper layer, of the topsheet comprises a hydrophobic, liquid permeable apertured polymeric film. Preferably, the upper layer is provided by a film material having apertures, which are provided to facilitate liquid transport from the wearer-facing surface towards the absorbent structure. If present the lower layer preferably comprises a non-woven layer, an apertured formed film or an air laid tissue.

The term apertured polymeric topsheet as used herein refers to topsheets comprising at least one layer or a multiplicity of layers wherein at least one layer is formed from a continuous or uninterrupted film material wherein apertures are created. It has been surprisingly discovered that apertured polymeric film topsheets yield significantly better odor control than other types of topsheets such as for example thermal bonded nonwoven materials.

In general the apertured polymeric topsheet of the present invention is compliant, soft feeling, and non-irritating to the wearer's skin. Further, the topsheet is fluid pervious permitting fluids (e.g., menses and/or urine) to readily penetrate through its thickness. Suitable apertured polymeric film topsheets for use herein include polymeric apertured formed films, thermoplastic films, apertured plastic films, and hydroformed thermoplastic films; porous foams; net-like reticulated foams and thermoplastic films; and thermoplastic scrims.

Preferred topsheets for use in the present invention are selected from apertured formed film topsheets. Apertured formed films are especially preferred for the topsheet because they are pervious to body exudates and yet non-absorbent and have a reduced tendency to allow fluids to pass back through and rewet the wearer's skin. Thus, the surface of the formed film that is in contact with the body remains dry; thereby reducing body soiling and creating a more comfortable feel for the wearer. Suitable formed films are described in U.S. Pat. No. 3,929,135 (Thompson), issued Dec. 30, 1975; U.S. Pat. No. 4,324,246 (Mullane, et al.), issued Apr. 13, 1982; U.S. Pat. No. 4,342,314 (Radel. et al.), issued Aug. 3, 1982; U.S. Pat. No. 4,463,045 (Ahr et al.), issued Jul. 31, 1984; and U.S. Pat. No. 5,006,394 (Baird), issued Apr. 9, 1991. Each of these patents are incorporated herein by reference. Particularly preferred microapertured formed film topsheets are disclosed in U.S. Pat. No. 4,609,518 (Curro et al), issue Sep. 2, 1986 and U.S. Pat. No. 4,629,643 (Curro et al), issued Dec. 16, 1986, which are incorporated by reference. The preferred topsheet for the present invention is the formed film described in one or more of the above patents and marketed on sanitary napkins by The Procter & Gamble Company of Cincinnati, Ohio as "DRI-WEAVE."

Suitable topsheets in the field of three-dimensional formed film are described in EP 0 018 020 and EP 0 059 506. Especially preferred in a three dimensional formed polymeric topsheet having openings in the shape of regular pentagons which are regularly spaced and have an opening of 0.41 square millimeter. The openings are spaced 0.37 square millimeters apart transversely and 0.25 millimeters longitudinally. This topsheet has an initial opening (preforming) thickness of about 25 m a final (post forming) thickness of about 0.53 mm and an open area of from 25% to about 40%.

Another formed film topsheet which is especially preferred is one having openings of two shapes; regular pentagons having an area of about 0.21 square millimeters and an irregular hexagon having an area of 1.78 square millimeters. The openings are distributed so that the distance between the sides of the figures is about 0.37 mm to about 0.42 mm. The preforming and post forming film thickness are respectively 0.25 and 0.43 mm. This film has an open area of about 33.7%. Both films are made according to the teachings of the above-mentioned patents.

A third form suitable topsheet comprises two separate perforated polymeric films superimposed one on the other.

The body surface of the formed film topsheet of the present invention may also be hydrophilic so as to help liquid to transfer through the topsheet faster than if the body surface was not hydrophilic. In this manner the likelihood that menstrual fluid will flow off the topsheet rather than flowing into and being absorbed by the absorbent structure is diminished. In a preferred embodiment, surfactant is incorporated into the polymeric materials of the formed film topsheet such as is described in U.S. patent application Ser. No. 07/794,745, "Absorbent Article Having A Nonwoven and Apertured Film Coversheet" filed on Nov. 19, 1991 by Aziz, et al., which is incorporated by reference. Alternatively, the body surface of the topsheet can be made hydrophilic by treating it with a surfactant such as is described in the above referenced U.S. Pat. No. 4,950,254, incorporated herein by reference.

The Backsheet

The backsheet primarily prevents the extrudes absorbed and contained in the absorbent structure from wetting articles that contact the absorbent product such as underpants, pants, pyjamas and undergarments. The backsheet is preferably impervious to liquids (e.g. menses and/or urine) and is preferably manufactured from a thin plastic film, although other flexible liquid impervious materials can also be used. As used herein, the term "flexible" refers to materials that are compliant and will readily conform to the general shape and contours of the human body. The backsheet also can have elastic characteristics allowing it to stretch in one or two directions. In a preferred embodiment the backsheet comprises a first layer, which provides the garment-facing surface of the backsheet and a second layer (also called secondary backsheet) between the first layer and the absorbent structure/core.

The backsheet typically extends across the whole of the absorbent structure and can extend into and form part of or all of the preferred side flaps, side wrapping elements or wings.

The backsheet can comprise a woven or nonwoven material, polymeric films such as thermoplastic films of polyethylene or polypropylene, or composite materials such as a film-coated nonwoven material. Preferably, the backsheet is a polyethylene film typically having a thickness of from about 0.012 mm (0.5 mil) to about 0.051 mm (2.0 mil).

Exemplary polyethylene films are manufactured by Clopay Corporation of Cincinnati, Ohio, under the designation P18-0401 and by Ethyl Corporation, Visqueen Division, of Terre Haute, Ind., under the designation XP-39385. The backsheet is preferably embossed and/or matt finished to provide a more cloth like appearance. Further, the backsheet can permit vapors to escape from the absorbent structure, i.e. be breathable, while still preventing exudates from passing through the backsheet. Also breathable backsheets comprising several layers, e.g. film plus non-woven structures, can be used.

Suitable breathable backsheets for use herein include all breathable backsheets known in the art. In principle there are two types of breathable backsheets, single layer breathable backsheets that are breathable and impervious to liquids and backsheets having at least two layers, which in combination provide both breathability and liquid imperviousness.

Suitable single layer breathable backsheets for use herein include those described for example in GB A 2184 389, GB A 2184 390, GB A 2184 391, U.S. Pat. No. 4,591,523, U.S. Pat. No. 3,989,867 U.S. Pat. No. 3,156,242 and European Patent Application number 95120653.1.

Suitable dual or multi layer breathable backsheets for use herein include those exemplified in U.S. Pat. No. 3,881,489, U.S. Pat. No. 4,341,216, U.S. Pat. No. 4,713,068, U.S. Pat. No. 4,818,600, EPO 203 821, EPO 710 471, EPO 710 472, European Patent Application numbers 95120647.3, 95120652.3, 95120653.1 and 96830097.0.

Particularly preferred are backsheets meeting the requirements as defined in European Patent Application number 96830343.8 and more preferably wherein the absorbent article also meets the requirements as described therein.

According to the present invention the breathable backsheet comprises at least one, preferably at least two water vapor permeable layers. Suitable water vapor permeable layers include 2 dimensional, planar micro and macroporous films, monolithic films, macroscopically expanded films and formed apertured films. According to the present invention the apertures in said layer may be of any configuration, but are preferably spherical or oblong. The apertures may also be of varying dimensions. In a preferred embodiment the apertures are preferably evenly distributed across the entire surface of the layer, however layers having only certain regions of the surface having apertures are also envisioned.

2 dimensional planar films as used herein have apertures having an average diameter of from 5 micrometers to 200 micrometers. Typically, 2-dimensional planar micro porous films suitable for use herein have apertures having average diameters of from 150 micrometers to 5 micrometers, preferably from 120, micrometers to 10 micrometers, most preferably from 90 micrometers to 15 micrometers. Typical 2 dimensional planar macroporous films have apertures having average diameters of from 200 micrometers to 90 micrometers. Macroscopically expanded films and formed apertured films suitable for use herein typically have apertures having diameters from 100 micrometers to 500 micrometers. Embodiments according to the present invention wherein the backsheet comprises a macroscopically expanded film or an apertured formed film, the backsheet will typically have an open area of more than 5%, preferably from 10% to 35% of the total backsheet surface area.

Suitable 2 dimensional planar layers of the backsheet may be made of any material known in the art, but are preferably manufactured from commonly available polymeric materials. Suitable materials are for example GORE-TEX (TM) or Sympatex (TM) type materials well known in the art for their application in so-called breathable clothing. Other suitable materials include XMP-1001 of Minnesota Mining and Manufacturing Company, St. Paul, Minn., USA. As used herein the term 2 dimensional planar layer refers to layers having a depth of less than 1 mm, preferably less than 0.5 mm, wherein the apertures have an average uniform diameter along their length and which do not protrude out of the plane of the layer. The apertured materials for use as a backsheet in the present invention may be produced using any of the methods known in the art such as described in EPO 293 482 and the references therein. In addition, the dimensions of the apertures produced by this method may be increased by applying a force across the plane of the backsheet layer (i.e. stretching the layer).

Suitable apertured formed films include films, which have discrete apertures, which extend beyond the horizontal plane of the garment-facing surface of the layer towards the core thereby forming protuberances. The protuberances have an orifice located at their terminating ends. Preferably said protuberances are of a funnel shape, similar to those described in U.S. Pat. No. 3, 929,135. The apertures located within the plane and the orifices located at the terminating end of protuberance themselves maybe circular or non circular, provided the cross sectional dimension or area of the orifice at the termination of the protuberance is smaller than the cross sectional dimension or area of the aperture located within the garment facing surface of the layer. Preferably said apertured preformed films are unidirectional such that they have at least substantially, if not complete one directional fluid transport towards the core. Suitable macroscopically expanded films for use herein include films as described in for example in U.S. Pat. No. 637,819 and U.S. Pat. No. 4,591,523.

Suitable macroscopically expanded films for use herein include films as described in for example U.S. Pat. No. 4,637,819 and U.S. Pat. No. 4,591,523.

Suitable monolithic films include Hytrel™, available from DuPont Corporation, USA, and other such materials as described in Index 93 Congress, Session 7A "Adding value to Nonwovens", J-C. Cardinal and Y. Trouilhet, DuPont de Nemours International S.A., Switzerland.

According to the present invention the backsheet may comprise in addition to said water vapor permeable layer additional backsheet layers. Said additional layers may be located on either side of said water vapor permeable layer of the backsheet. The additional layers may be of any material, such as fibrous layers or additional water vapor permeable layers as described herein above.

Odor Control Test

The odor reduction is measured by for example an in vitro sniff test. In vitro sniff test consists in analyzing by expert graders the odor associated with articles comprising the ingredients to be tested (including references articles) when contacted with an odorous components-containing solution The expert graders express their judgment about (un) pleasantness of the odor using a (un)pleasantness scale, typically from −10 (highest level of unpleasantness) to 5 (most pleasant). With this procedure, each grader compares MU (Unpleasantness) in the test session. The relative MU odor values from different products are assigned numbers. For example, in a test session, a sample that is perceived to be twice as strong as another is assigned twice as large a number. One that is perceived to be one-tenth as strong as another is assigned a number one-tenth as large, etc. In each test session, zero is used to designate neutral hedonicity, and + and − numbers are assigned in ratio proportion to the relative pleasantness and unpleasantness of the odor.

Surprisingly in vitro in-house sniff tests conducted by using an in-house odorous components-containing solution reproducing the essential malodorous characteristics of menses showed synergistic odor reduction when comparing chitosan (e.g. chitosonium pyrrolidone carboxylate (Kytamer®) together with an odor controlling agent according to the present invention (e.g., zeolite A, Wessalith CS, available from Degussa AG, or ethylenediamine tetracetate (BASF) or hydroxypropyl beta-cyclodextrin (Fluka)) to each of these ingredients taken alone at the same total level of active. Indeed the % of unpleasantness reduction obtained for the mixture was higher than the % of unpleasantness reduction obtained for each of the two ingredients used alone at the same total level of active. The Unpleasantness values, for each sample, were obtained as a mean of at least 15 observations (3 products, 5 graders). These results were statistically significant.

Alternatively the odor reduction can also be measured with in vivo sniff tests as described in patent applications, EP-A-811387 or WO97/4619 1, herein incorporated by reference. The present invention is further illustrated by the following examples.

EXAMPLES

Example A

The feminine pads used in the following examples were Always (Always is a registered Trade Mark) as sold by the Procter & Gamble Company.

Each feminine pad was opened by cutting the wrap around the perforated coverstock at its bottom face approximately along a longitudinal edge of the release paper, which covers the external adhesive layer. The side of the absorbent fibrous core was then exposed by slightly shifting the water impermeable plastic bottom layer and subsequently, the fibrous core was split into two halves, each having approximately the same thickness, along a plane, which is parallel to the plane of the pad itself. Chitosan material and odor controlling agent were homogeneously distributed between the two fibrous layers.

The water impermeable inner backsheet was then put back into its original position and the wrap around perforated coverstock was sealed along the cut by means of e.g. a double-sided adhesive tape.

The chitosan powder material used was 0.2 g of chitosonium pyrrolidone carboxylate, commercially available from Amerchol Corporation, Edison, N.J. under the name Kytamer® PC.

The odor-controlling agent used was 0.3 g of Zeolite A, Wessalith CS, available from Degussa AG.

Example B

Other pads were prepared by following the method in Example A except that the odor-controlling agent used was cyclodextrin instead of zeolite. The cyclodextrin used was 0.1 g of hydroxypropyl beta-cyclodextrin commercially available from Fluka.

Example C

Other pads were prepared by following the method in Example A except that the odor-controlling agent used was a chelating agent instead of zeolite. The chelating agent used was 0.1 g of ethylenediamine tetracetate commercially available from BASF AG.

Examples D, E and F

Other pads were prepared by following the method in respectively Examples A, B, and C except that an absorbent gelling material (AGM) was homogeneously distributed between the two fibrous layer beside the chitosan material and odor controlling agent used respectively in Examples A, B and C.

The AGM used was 0.4 g of cross-linked sodium polyacrylate Xz 9589001, available from Dow Chemicals.

Examples G, H and I

Other pads were prepared by following the method in respectively Examples A, B and C except that after having split the fibrous core into two halves, an absorbent gelling material (AGM) and the odor controlling agent as defined in respectively Examples A, B and C, were respectively homogeneously distributed between the two halve fibrous layers and the chitosan material was homogeneously distributed onto the lower halve fibrous layer (i.e., the one intended to be closer to the backsheet of the pad once reconstituted). Actually a solution of chitosan material was prepared and homogeneously sprayed onto the inner side of the lower halve fibrous layer.

The chitosan solution was prepared by solubilizing 1 g of chitosonium pyrrolidone carboxylate commercially available from Amerchol Corporation under the name Kytamer® PC in 100 g of distilled water and stirring at 40° C. over 1 night. 10 g of the prepared solution was sprayed onto the lower halve of the fibrous layer (i.e., 0.1 g of chitosan per pad) AGM used was 0.4 g of cross-linked sodium polyacrylate, commercially available from Dow Chemicals (code:XZ 9589001).

The odor controlling agents used (type and amount) were the ones respectively defined in Examples A, B and C.

Accordingly various pads were made respectively corresponding to Examples G, H and I with different odor controlling agents, corresponding respectively to the odor controlling agents used in Examples A, B and C described herein above.

Example J

The feminine pantiliner used in the following examples is a modified panty liner based on Always "Alldays Duo Active" manufactured by Procter & Gamble, Germany. The topsheet is a film/non woven composite {film supplier code BPC 5105 CPM BP Chemical Germany, non-woven supplier code ARBO TB/BI Mequinenza Spain}. The core material is a tissue laminate (13.2 cm×4.0 cm) composed of a 2 layers of air laid tissue of 55 g/m² basis weight {available from Unikay Italy under the supplier code Unikay 303 LF}. Between the two tissue layers the laminate contains chitosan material together with an odor-controlling agent.

The backsheet comprises two layers a first layer and a second layer. The first layer is in contact with the absorbent tissue and the second layer. The second layer is in contact with the first layer and the undergarment of the wearer. The first layer is a formed apertured film (CPT) made of Low Density PE {supplied by Tredegar Film Products B. V. Holland under the manufacturing code X-1522}. The second layer is composed of a nonwoven laminate {13 MB/16 SB manufactured by Corovin GmbH in Germany under the trade name MD 2005}. The nonwoven laminate is composed of 16 g/m² spun bond and 13 g/m² meltblown. Each backsheet layer is joined over the full surface by an extensively overlapped spiral glue application at a basis weight of approximately 8 g/m². The glue utilized for attachment of both backsheet layers was supplied by SAVARE' SpA. Italy (under the material code PM 17).

The chitosan material used was 0.2 g of chitosonium pyrrolidone carboxylate, commercially available from Amerchol Corporation, Edison, N.J. under the name Kytamer® PC.

The odor controlling agent used was either 0.3 g of Zeolite A, Wessalith CS, available from Degussa AG, or 0.1 g of hydroxypropyl beta-cyclodextrin commercially available from Fluka, or 0.1 g of ethylenediamine tetracetate (EDTA) commercially available from BASF AG.

Other panty liners can be made starting from the ones exemplified in Example J above except that AGM is incorporated on top of the chitosan material and odor-controlling agent. Indeed the 3 classes of ingredients were homogeneously mixed together to obtain a powder that was homogeneously distributed between the two layers of the laminate. AGM used was 0.4 g of cross-linked sodium polyacrylate, commercially available from Dow Chemicals (code:XZ 9589001).

All the above exemplified pads and pantiliners delivered outstanding odor control properties towards malodorous compounds associated with bodily fluids.

What is claimed is:

1. A disposable absorbent article comprising a liquid pervious topsheet, a backsheet and an absorbent core intermediate to said backsheet and said topsheet; said absorbent core comprising an odour control system for controlling odours comprising a cationic polysaccharide together with an odor controlling agent; wherein said cationic polysaccharide is an aminopolysaccharide selected from the group consisting of chitosan, chitosan salt, chitosans that comprise carboxymethyl, memylpyrrolldinone or glycol pendant groups on a glucan chain, crosslinked chitosan and mixtures thereof.

2. An article according to claim 1 wherein said chitosan has a degree of deacetylation of more than 75%.

3. An article according to claim 1 wherein the cationic polysaccharide is selected from the group consisting of a chitosan salt of citric acid, formic acid, acetic acid, N-acetylglycine, acetylsalicylic acid, fumaric acid, glycolic acid, iminodiacetic acid, itaconic acid, lactic acid, maleic acid, malic acid, nicotinic acid, salicylic acid, succinamic acid, succinic acid, ascorbic acid, aspartic acid, glutamic acid, glutaric acid, malonic acid, pyruvic acid, sulfonyldiacetic acid, benzoic acid, epoxysuccinic acid, adipic acid, thiodiacetic acid, thioglycolic acid, alanine, valine, leucine, isoleucine, prolinephenylalanine, triptofane, metionine, glycine, serine, cysteine, tyrosine, asparagine, glutamine, lysine, arginine, histidine, hydroxyproline, pyrrolidone carboxylic acid, chitosonium pyrrolidone carboxylate and mixtures thereof.

4. An article according to claim 1 which comprises from about 0.5 $gm^{-2}$ to about 500 $gm^{-2}$ of cationic polysaccharide.

5. An article according to claim 1 wherein the odor controlling agent is a chelating agent and/or an odor absorbent agent.

6. An article according to claim 5 wherein said odor controlling agent is an odor absorbent agent selected from the group consisting of zeolites, carbons, diatomaceous earth, starches, cyclodextrin, kieselguhr, clays, ion exchange resins and combination thereof and preferably is zeolite, aipha-cyclodextrin, beta-cyclodextrin, gamma-cyclodextrin or a combination thereof.

7. An article according to claim 5 wherein the odor controlling agent is a chelating agent selected from the group consisting of phosphonate chelating agents, amino phosphonate chelating agents, polyfunctionally-substituted aromatic chelating agents, animo carboxylate chelating agents, ethylene diamine N,N'-disuccinic acid, aspartic acid, glutamic acid, malonic acid, glycine and mixtures thereof.

8. An article according to claim 7 wherein the chelating agent is selected from the group consisting of ethylene diamine tetracetate, -triacetate, -diacetate, and -monoacetate, ethylenediamine N,N,-disuccinic acid, ethylenediamine penta methylene phosphonic acid, ethylenediamine tetra methylene phosphonic acid and mixtures thereof.

9. An article according to claim 1 which comprises from about 1 to about 600 $gm^{-2}$ of the odor controlling agent.

10. An article according to claim 1 further comprising an absorbent gelling material.

11. An article according to claim 5 further comprising an absorbent gelling material.

12. An article according to claim 10, wherein the absorbent gelling material is present at a level from about 5 $gm^{-2}$ to about 250 $gm^{-2}$.

* * * * *

UNITED STATES PATENT AND TRADEMARK OFFICE
CERTIFICATE OF CORRECTION

PATENT NO. : 6,960,655 B2
DATED : September 10, 2002
INVENTOR(S) : Achille Di Cintio et al.

It is certified that error appears in the above-identified patent and that said Letters Patent is hereby corrected as shown below:

Column 13
Lines 46 and 52, "quatemary" should read -- quaternary --.

Column 28,
Line 48, "memylpyrrolldinone" should read -- memylpyrolldinone --.

Column 29,
Line 12, "aipha" should read -- alpha --.

Signed and Sealed this

Eleventh Day of April, 2006

JON W. DUDAS
*Director of the United States Patent and Trademark Office*

UNITED STATES PATENT AND TRADEMARK OFFICE
CERTIFICATE OF CORRECTION

PATENT NO. : 6,960,655 B2
DATED : November 1, 2005
INVENTOR(S) : Achille Di Cintio et al.

It is certified that error appears in the above-identified patent and that said Letters Patent is hereby corrected as shown below:

Column 13
Lines 46 and 52, "quatemary" should read -- quaternary --.

Column 28,
Line 48, "memylpyrrolldinone" should read -- memylpyrolldinone --.

Column 29,
Line 12, "aipha" should read -- alpha --.

This certificate supersedes Certificate of Correction issued April 11, 2006.

Signed and Sealed this

Second Day of May, 2006

JON W. DUDAS
*Director of the United States Patent and Trademark Office*